United States Patent [19]

Takeuchi

[11] 4,288,882
[45] Sep. 15, 1981

[54] ENDOSCOPE SHEATH CLEANING DEVICE

[75] Inventor: Haruo Takeuchi, Fuchu, Japan

[73] Assignee: Olympus Optical Co., Ltd., Tokyo, Japan

[21] Appl. No.: 110,756

[22] Filed: Jan. 9, 1980

[30] Foreign Application Priority Data

Jan. 17, 1979 [JP] Japan ................................ 54/4080

[51] Int. Cl.³ ........................ B08B 9/02; B08B 3/02; A46B 13/04
[52] U.S. Cl. ..................................... 15/88; 15/21 C; 15/97 R; 134/199
[58] Field of Search .................... 15/21 B, 21 C, 21 D, 15/88, 59, 65, 97 R, 104.04; 422/1; 134/199, 184; 128/4

[56] References Cited

U.S. PATENT DOCUMENTS

| | | | |
|---|---|---|---|
| 3,761,984 | 10/1973 | Hauschild et al. | 15/21 D |
| 3,936,900 | 2/1976 | Bende | 15/88 |
| 4,064,886 | 12/1977 | Heckele | 134/184 |

Primary Examiner—Edward L. Roberts

[57] ABSTRACT

An endoscope sheath cleaning device comprises an upper plate, a hole formed in the upper plate to allow for the insertion of an endoscope sheath into the cleaning device, a nozzle head disposed under the hole, an endoscope sheath cleaning mechanism which includes brushes or spongy cleaning members and is set under the nozzle head, a rotation mechanism for the cleaning mechanism, a J-shaped or vertically straight endoscope sheath guiding tube, one end of which is set concentric with the endoscope sheath insertion hole, and a drain tube branched from the lowest part of the endoscope sheath guiding tube. An annular jet chamber is formed in the cylindrical nozzle head. The nozzle head is penetrated by a plurality of nozzles whose nozzle openings are projected into the jet chamber, and which are directed so as to cause a washing liquid to be ejected over the endoscope sheath cleaning mechanism. The endoscope sheath is repeatedly taken into and out of the guiding tube through the insertion hole. The peripheral surface of the endoscope sheath is more quickly and reliably cleaned, as the repeated up and down movements of the endoscope sheath through the guiding tube continue. Where running water is used as a washing liquid, not only cleaning but rinsing as well can be easily carried out without providing any other extra means than the cleaning device itself.

15 Claims, 10 Drawing Figures

ENDOSCOPE SHEATH CLEANING DEVICE

BACKGROUND OF THE INVENTION

This invention relates to an endoscope sheath cleaning device.

According to the prior art device for cleaning a flexible endoscope sheath, an endoscope sheath to be cleaned was set on a support frame in the spiral form, and a washing liquid was ejected on the surface of the endoscope sheath from revolving spray nozzles set above and below the support frame. In this case, however, only the limited surface portions of the endoscope sheath were sprayed with a washing liquid, with the result that the remaining surface portions were insufficiently washed, making it often necessary to undertake rewashing in order to full clean the whole surface area of the endoscope sheath.

The conventional endoscope sheath cleaning device had further disadvantages that the soiled endoscope sheath had to be manually wound in the helical form, imparting an unpleasant feeling to the operator, and moreover said winding consumed a great deal of time with the resultant decline in the cleaning efficiency.

SUMMARY OF THE INVENTION

The object of this invention is to provide an endoscope sheath cleaning device which allows for the easy, reliable fitting and removal of the endoscope sheath, makes it possible to recognize the cleaned condition of the surface of the endoscope sheath during washing, and further enables the whole peripheral surface of the endoscope sheath to be uniformly cleaned.

An endoscope sheath cleaning device of this invention comprises a housing whose upper plate is provided with a hole through which an endoscope sheath is inserted into the cleaning device, a cylindrical nozzle head which is fixed to the underside of said upper plate and in which an annular jet chamber is formed with a larger inner diameter than the outer diameter of the endoscope sheath, a plurality of spray nozzles which are equidistantly arranged on the lateral wall of the circular nozzle head in the circumferential direction, and are each provided with a nozzle opening radially directed to the interior of the jet chamber, thereby spraying a washing liquid uniformly all over the peripheral surface of the endoscope sheath, endoscope sheath cleaning means disposed under the nozzle head to resiliently touch the peripheral surface of the endoscope sheath, rotation means set concentric with the jet chamber to rotate said endoscope sheath cleaning means, a guide tube, one end of which concentrically communicates with said jet chamber, and whose intermediate part at least adjacent to said one end extends downward from said one end, and a drain tube which is branched from the lowermost part of said guide tube to drain off a used washing liquid.

In operation, a washing liquid is ejected from the spray nozzles. While the endoscope sheath cleaning means is rotated, the endoscope sheath to be washed is inserted into the guide tube through the hole formed in the upper plate of the housing. Where necessary, the endoscope sheath is repeatedly moved up and down. The above-mentioned steps enable the soiled peripheral surface of the endoscope sheath to be cleaned easily, quickly and reliably.

BRIEF DESCRIPTION OF THE DRAWINGS

This invention can be fully understood from the following detailed description with reference to the accompanying drawings, in which.

DETAILED DESCRIPTION OF THE PREFERRED EMBODIMENTS

Figure 1:
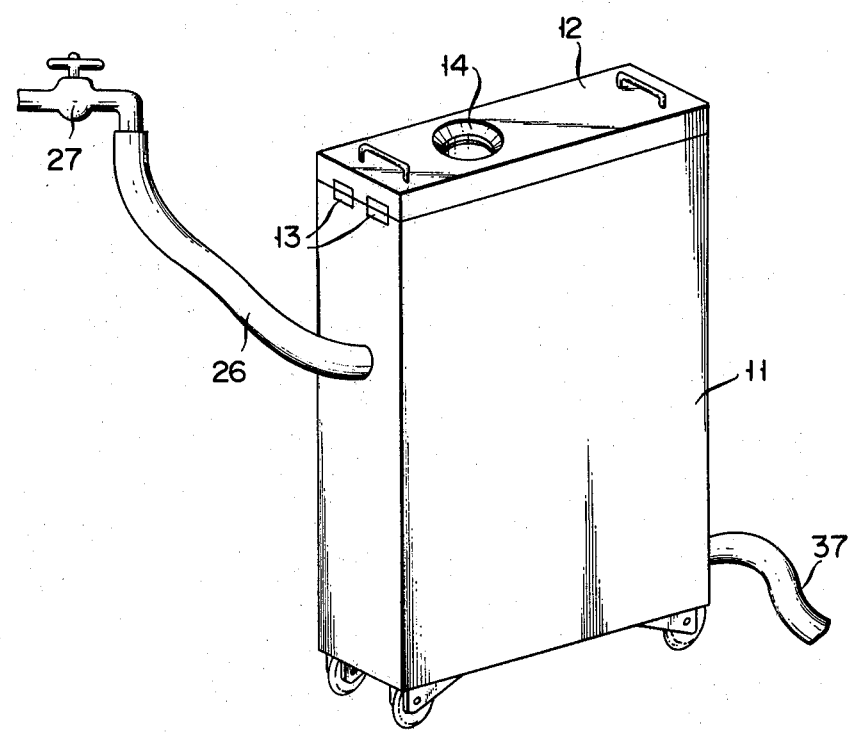
FIG. 1 is an oblique view of the whole of an endoscope sheath cleaning device embodying this invention.
Figure 2:
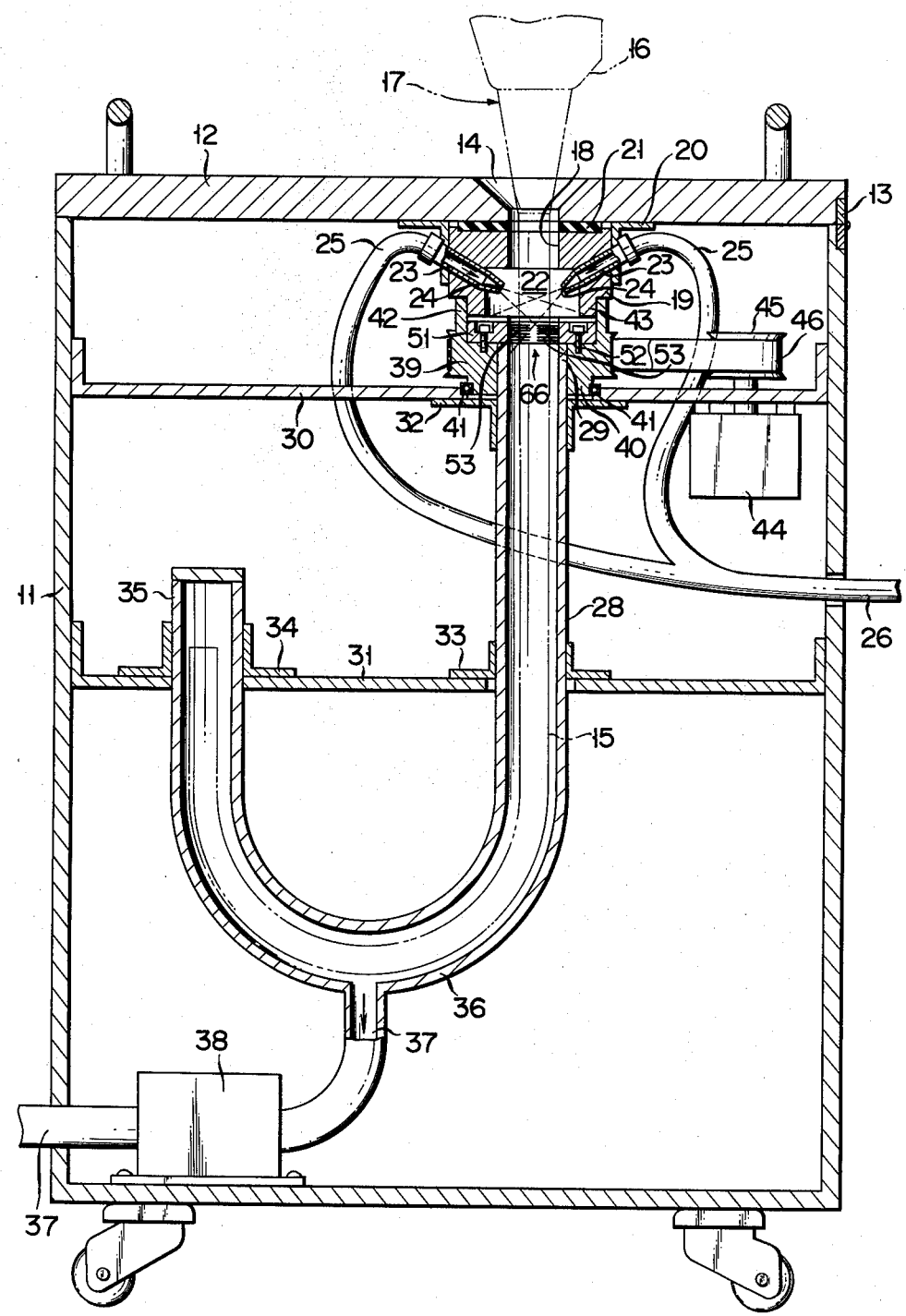
FIG. 2 is a longitudinal cross-sectional view of FIG. 1.

Referring to FIGS. 1 and 2, an endoscope sheath cleaning device embodying this invention comprises a housing 11, and an upper plate 12 which is swingably fitted to the top side of the housing 11 by means of hinges 13 normally to close the opening of said top side. The upper plate 12 is provided with an inverter round conical hole 14. The lower end of the hole 14 has a sufficiently large diameter to allow for the free passage of a sheath 15 connected to the operation section 16 of an endoscope 17 such as an endoscope for large intestines (or colonofiberscope).

A cylindrical nozzle head 19 (FIG. 3) has a cylindrical bore 18 having substantially the same diameter as the lower end of the inverted round conical hole 14 and set concentric with the hole 14. The cylindrical nozzle head 19 is fixed to the underside of the upper plate 12 by means of a ring-shaped, flanged fixing member 20 with seal packing such as rubber interposed between the nozzle head 19 and the upper plate 12.

Figure 3:
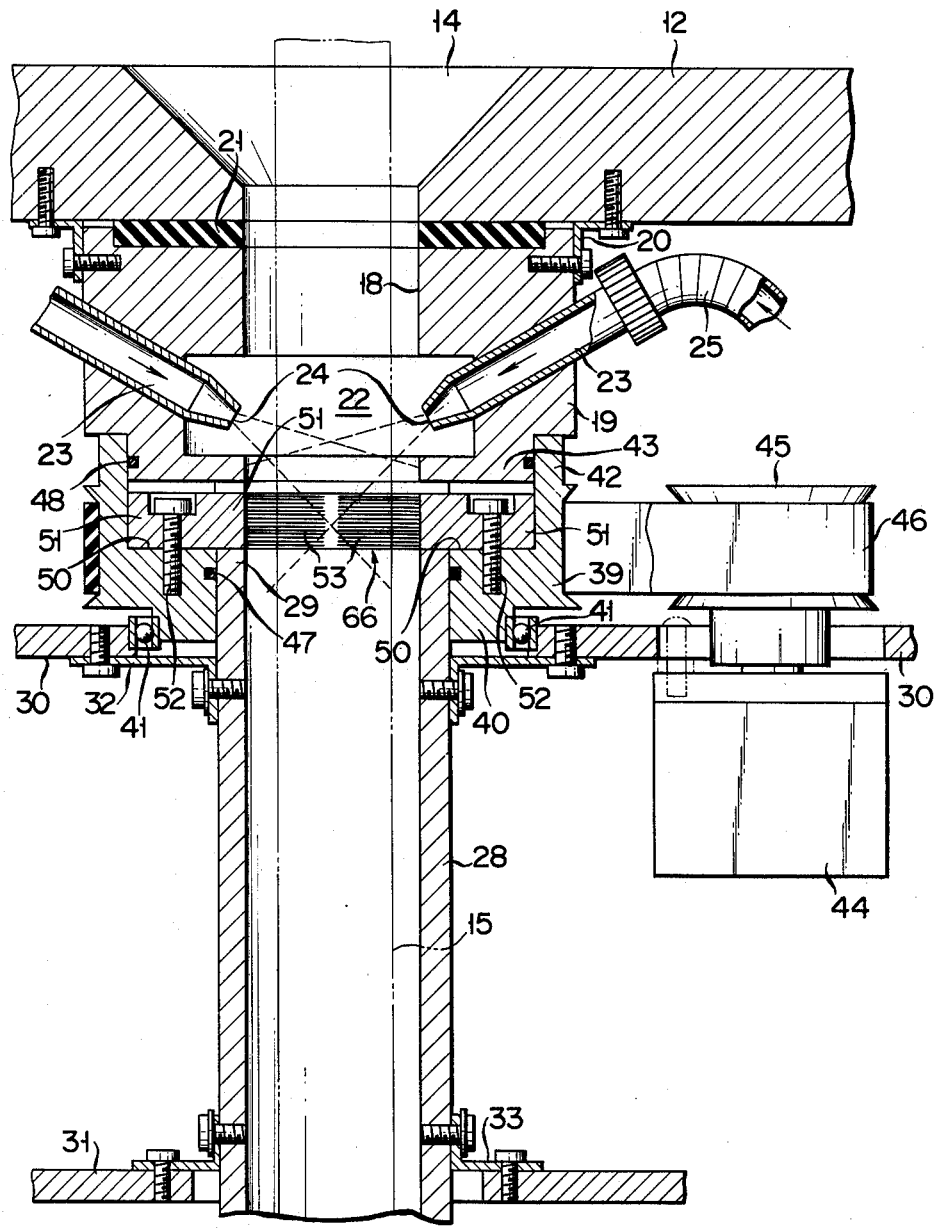
FIG. 3 is an enlarged sectional view of the main part of FIG. 2.

Referring to FIG. 3, an annular jet chamber 22 is formed in the lower part of the nozzle head 19 with a larger diameter than the cylindrical bore 18 and in a state disposed concentric with the bore 18.

A plurality of nozzles 23 are arranged in the lateral wall of the cylindrical nozzle head 19 equidistantly in the circumferential direction and extend throughout the lateral wall. The nozzle openings 24 of the respective nozzles 23 are inclined downward toward the axis of the jet chamber 22 to eject a washing liquid convergently over the peripheral surface of the endoscope sheath 15. Further, the nozzle openings 24 are set outside of the cylindrical bore 18 of the nozzle head 19 to prevent the endoscope sheath 15 from striking against the nozzle openings 24.

Referring to FIGS. 1 and 2, a washing liquid supplying apparatus is provided outside (sometimes inside) of an endoscope sheath cleaning device. Where water is used as a washing liquid, branch hoses 25 diverted from a main hose 26 extending from a running water cock 27 (FIG. 1) are connected to the rear ends of the corresponding nozzles 23. Further, an electromagnetic valve may be provided in the intermediate part of the main hose 26 to control the supply of a washing liquid from a washing liquid supplying apparatus and the interruption thereof.

A J-shaped guide tube 28 through which a flexible endoscope sheath 15 is inserted into the cleaning device has a larger inner diameter than the outer diameter of the endoscope sheath. The upper end portion 29 of the stem section of the J-shaped guide tube 28 is set concentric with the jet chamber 22. The upper end portion 29 is fixedly supported by an upper frame 30 and a lower frame 31 both horizontally extending in the housing 11 by means of fixing rings 32, 33. The blind other end portion 35 of the stem section of the J-shaped guide tube 28 is fixed to a lower frame 31 by means of a fixing ring 34. A drain tube 37 is branched from the bottom of the bend 36 of the guide tube 28 for communication with, for example, an exhaust liquid treating means set outside of the endoscope sheath cleaning device and sewage system.

Referring to FIGS. 2 and 3, a pulley 39 is rotatably mounted on the upper end portion 29 of the stem section of the J-shaped guide tube 28 in a state sealed by an O-ring 47. The pulley 39 is also rotatably supported on the upper frame 30 by means of a ball bearing 41 set between the upper frame 30 and a boss 40 of the pulley 39 having a smaller diameter than the main body of the pulley 39. A sleeve portion 42 is provided on the upper surface of the pulley 39 for receiving a smaller diameter section 43 in the lower part of the nozzle head 19. A seal O-ring 48 is disposed between the sleeve portion 42 and the smaller diameter section 43 of the nozzle head 19 to seal the jet chamber 22. Mounted on the upper frame 30 are an electric motor 44 and a pulley 45 driven thereby. A belt 46 is stretched across both pulleys 39 and 45, causing the pulley 39 to be driven by the motor 44. The pulleys 39, 45, motor 44 and belt 46 collectively constitute rotation means.

Figure 4:
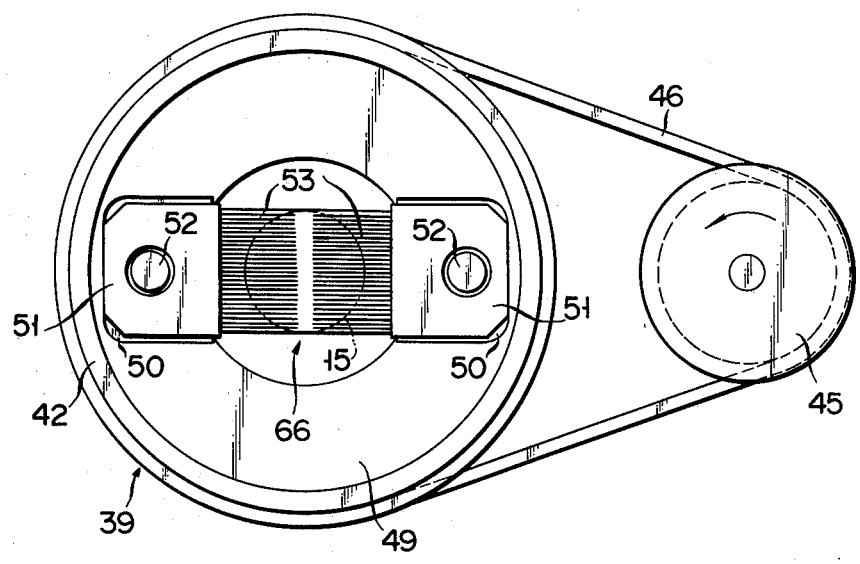
FIG. 4 is a plan view of a rotation mechanism in FIG. 2.
Figure 5:
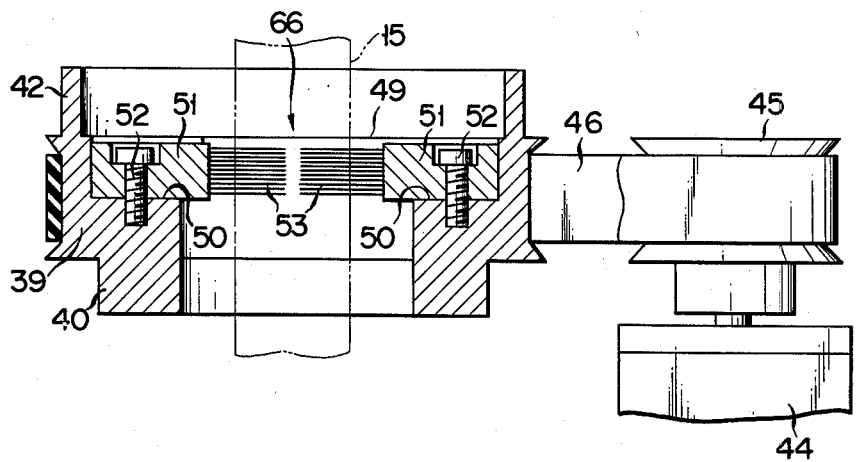
FIG. 5 is a vertical cross-sectional view of FIG. 4.

Referring now to FIGS. 3 to 5, a pair of recesses 50 are formed in the upper portion 49 of the pulley 39. A pair of plate-like brush holders 51 are placed into the respective recesses 50 and each fixed to the pulley 39 by a bolt 52.

A bundle of brush hairs 53 such as pig hairs or those of polytetrafluoroethylene is fitted to the respective brush holders 51. The hair bundles 53 of both brush holders 51 face each other.

The mutually facing end portions of the paired hair bundles 53 are positioned in the central opening of the upper surface 49 of the pulley 39 into which an endoscope sheath 15 to be washed is brought. Both brush holders 51 including the hairs 53 jointly constitute a brush unit 66 for cleaning the endoscope sheath 15.

The nozzle openings 24 are convergently directed toward the brush hairs 53, as shown in FIGS. 2 and 3 to eject a washing liquid directly over said brush hairs 53.

In operation, the electric motor 44 is first driven to rotate the brush unit 66. A washing liquid such as water, aqueous solution of neutral detergent, disinfecting liquid prepared from glutaraldehyde or formaldehyde, or any other cleaning material is sent forth to the nozzles 23 from a washing liquid supplying apparatus through the main tube 26 and the branch hoses 25. The washing liquid is sprayed over the bundles of brush hairs 53 through the nozzle openings 24.

Thereafter, an endoscope sheath 15 to be washed is gradually inserted into the guide tube 28 through the inverted round conical hole 14 with the distal end of the endoscope sheath 15 kept forward. Upon completion of the insertion, the endoscope sheath 15 is drawn out. While said insertion and withdrawal are repeated by hand or a proper known device, the peripheral surface of the endoscope sheath 15 is cleaned by the paired bundles of brush hairs 53, while a washing liquid is ejected over said peripheral surface through the nozzle openings 24. The used washing liquid falls through the guide tube 28 into the drain tube (or discharge tube) 37, and is drained out of the endoscope sheath cleaning device by actuating a discharge pump 38 or without applying the pump 38.

It is preferred that the brushes 53 be detachably set in the recesses 50 formed in the upper surface of the pulley 39. The reason for this is that where soils are deposited on the brush hairs 53 too tightly to be easily taken off, or the brush hairs 53 themselves fall off excessively to reduce the efficiency of the subject endoscope sheath cleaning device, the brush unit 66 can be easily replaced by fresh ones simply by opening the upper plate 12 without removing the nozzle head 19 and other associated members.

Figure 6:
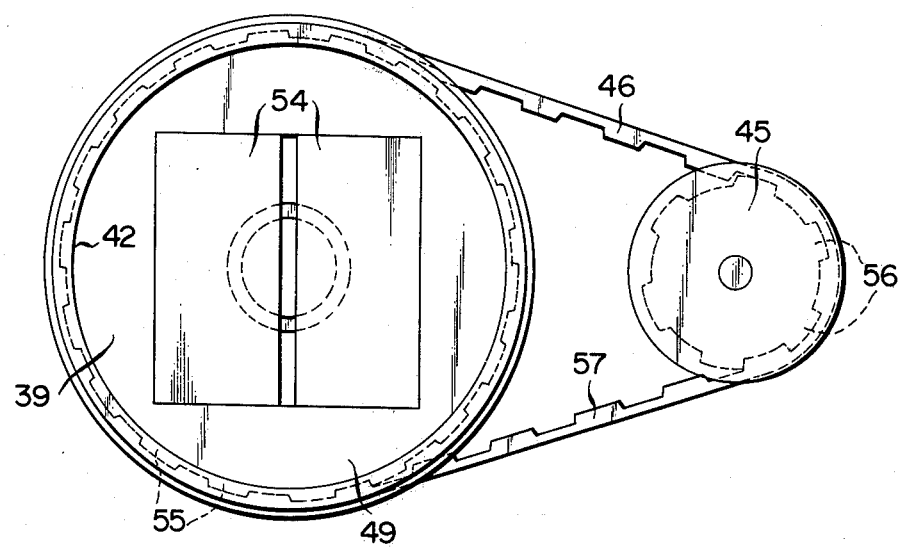
FIG. 6 is a plan view of a modification of a rotation mechanism.
Figure 7:
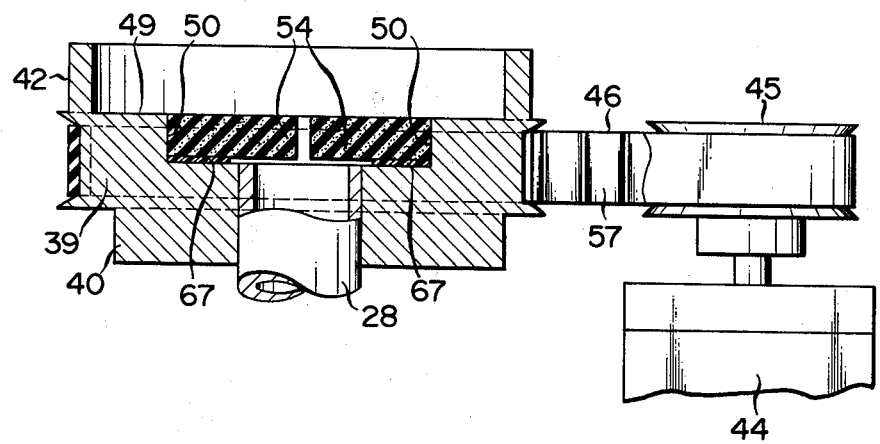
FIG. 7 is a vertical cross-sectional view of FIG. 6.

With an endoscope sheath cleaning device according to a second embodiment of FIGS. 6 and 7, a brush unit 66 constituted by the paired brush holders 51 and brush hairs 53, which is used in a rotation mechanism according to the first embodiment of FIGS. 4 and 5 is replaced by a pair of plate-like cleaning members 54 made of spongy material such as polyurethane foam. The outer peripheries of the pulleys 39, 45 are respectively provided with teeth 55, 56 as shown in FIG. 6. A timing or toothed belt 46 provided with teeth 57 engageable with recesses defined between the respective adjacent teeth 55, 56 of pulleys 39, 45 is stretched across the pulleys 39, 45.

The paired spongy plate-like cleaning members 54 are held in recesses 50 formed in the upper surface 49 of the pulley 39 by means of, for example, velvet fasteners 67 commonly known as magic tapes. The spongy plate-like cleaning members 54 almost uniformly contact the peripheral surface of the endoscope sheath 15 in a manner to wrap it, thereby preventing said peripheral surface from being forcefully rubbed or damaged. The toothed or timing belt 46 is used to exactly transmit the rotation force of the electric motor 44 to the pulley 39 whose periphery is also toothed as previous described.

There will now be described by reference to FIGS. 8 to 10 a rotation mechanism according to a third embodiment of this invention. With this third embodiment, the pulley 39, belt 46 and pulley 45 used in the first embodiment of FIGS. 4 and 5 are replaced by a gear wheel 58, an idling gear 59, and a gear wheel 60 engaged with each other in the order mentioned. The gear wheel 58 comprises an upward extending sleeve portion 61 which corresponds to the sleeve portion 42 of the first embodiment of FIGS. 4 and 5. The bottom 62 of the sleeve portion 61 (or the upper surface of the gear wheel 58) is provided with a ring-shaped mounting member 63, in which a pair of diametrically opposite mounting holes 64 are formed. These holes 64 are engaged with protuberances 65 formed on the surface 62 of the gear wheel 58, thereby causing the mounting member 63 to be securely set in position in the surface 62 of the gear wheel 58.

A brush unit 66 having the same construction as that of FIGS. 4 and 5 is fixed to the upper surface of the fitting member 63 with the paired bundles of brush hairs 53 set so as to face each other.

Figure 8:
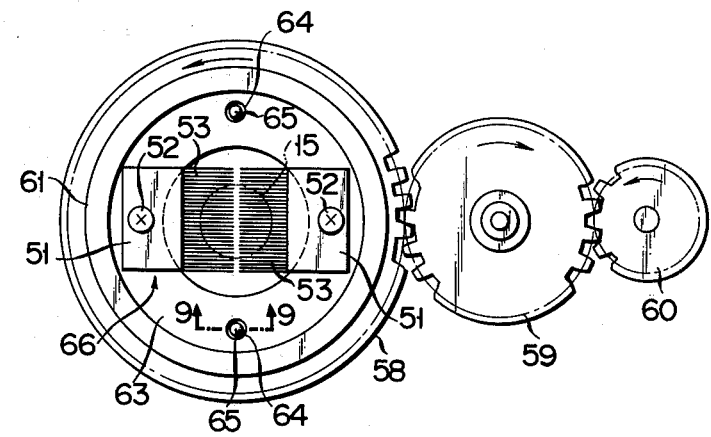
FIG. 8 is a plan view of a further modification of the rotation mechanism.
Figure 9:
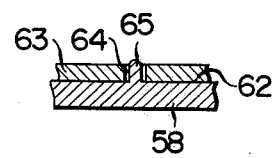
FIG. 9 is a cross-sectional view on line 9—9 of FIG. 8.
Figure 10:
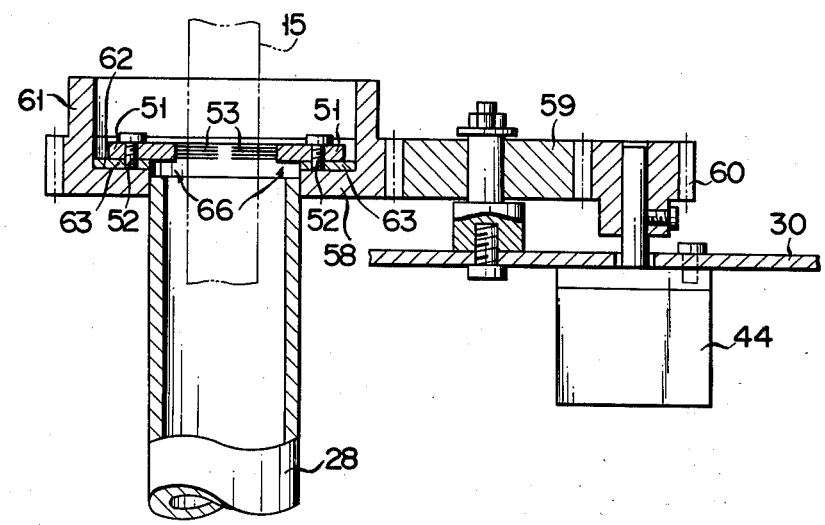
FIG. 10 is a vertical cross-sectional view of FIG. 8.

With an endoscope sheath cleaning device according to a third embodiment of FIGS. 8 to 10, the cleaning means can be fitted to the gear wheel 58 and removed therefrom easily by the so-called one-touch operation, facilitating the replacement of the cleaning means.

The endoscope sheath is generally chosen to have a length ranging from 250 to 1,500 millimeters and a diameter ranging from 4 to 16 millimeters. The dimensions of the various sections of the endoscope sheath cleaning device are defined in accordance with the size of an endoscope sheath to be cleaned. The inner diameter of the guide tube should obviously vary with the outer diameter of the endoscope sheath to be cleaned. In this case, the inner diameter of the guide tube should advisably be 5 to 15 millimeters larger than the outer diameter of the endoscope sheath. Referring to, for example, a colonofiberscope which is 1,000 millimeters in length and 13 millimeters in diameter, the radius of curvature of the bend of the J-shaped guide tube is preferred to be, for example, 50 millimeters.

According to this invention, the peripheral surface of the endoscope sheath 15 is cleaned by being uniformly and repeatedly rubbed by the brush unit 66. Therefore, the endoscope sheath cleaning device embodying the invention has the advantages that a far higher cleaning efficiency is ensured than the prior art cleaning device which simply ejects a washing liquid; even if a washing liquid is sprayed from the nozzle openings 24 at a reduced pressure, no difficulties will arise in cleaning the peripheral surface of the endoscope sheath; and where running water is applied as a washing liquid, the object of cleaning can be well attained simply by connecting the main hose to a water cock without using a water pump. Obviously, application of a washing liquid-pressurizing device such as a water pump more noticeably elevates the efficiency of the endoscope sheath cleaning device of this invention. Therefore, such a water pump or the like need not be excluded from use from the standpoint of this invention.

Where running water is used as a washing liquid, the brush hairs 53 or spongy cleaning members 54 are continuously supplied with fresh streams of water. Therefore, the endoscope sheath 15 finally taken out of the cleaning device may be regarded as automatically rinsed.

Further advantages of this invention are that since the endoscope sheath is cleaned simply by being repeatedly moved up and down, the cleaned condition of the sheath can be recognized by observing that part of the sheath which has been pulled out of the cleaning device, thereby effecting quick reliable cleaning without stopping the cleaning device or providing and extra means for observing the cleaned condition of the sheath 15; and a soiled endoscope sheath 15 is placed in a cleaning device by being conducted through a guide tube in a state just as taken out of, for example, the coeliac cavity of a patient instead of manually winding the sheath as has been the case with the prior art cleaning device, thereby minimizing the unpleasant feeling which might other be imparted to the operator, and enabling him to bundle the cleaning device with great ease.

The foregoing description refers to the case where a flexible endoscope sheath was washed and cleaned. However, the sheath may be of the rigid type. The only requirement in this case is that a straight guide tube be provided.

What is claimed is:
1. An endoscope sheath cleaning device comprising:
a housing;
an upper plate covering the housing;
an insertion hole formed in the upper plate to allow for insertion of an endoscope sheath into the cleaning device;
a nozzle head disposed under the upper plate and having a lateral wall;
endoscope sheath cleaning means disposed under the nozzle head to resiliently contact a peripheral surface of an endoscope sheath inserted into the cleaning device through the insertion hole;
nozzles provided in the lateral wall of the nozzle head and each having a nozzle opening directed to the endoscope sheath cleaning means;
rotation means for rotating the endoscope sheath cleaning means;
a guide tube disposed in the housing and having two ends with one end positioned higher than the other end and aligned with the insertion hole, said guide tube having a lower portion; and
a drain tube connected to the lower portion of the guide tube for draining a washing liquid in the guide tube.

2. The endoscope sheath cleaning device according to claim 1, wherein said endoscope sheath cleaning means comprises cleaning members made of a resilient material and mounted on the rotation means.

3. The endoscope sheath cleaning device according to claim 2, wherein said cleaning members are brushes.

4. The endoscope sheath cleaning device according to claim 3, wherein said endoscope sheath cleaning means includes a pair of brush holders mounted oppositely to each other on the rotation means and fitted with said brushes so as to face each other.

5. The endoscope sheath cleaning device according to claim 4, wherein said endoscope sheath cleaning means comprises a mounting member to which the brush holder are fixed; and engagement means is provided between the rotation means and mounting member to securely set the mounting member in position on the rotation means.

6. The endoscope sheath cleaning device according to claim 5, wherein said engagement means comprises engagement holes formed in the mounting member and protuberances formed on the rotation means to be inserted into engagement holes.

7. The endoscope sheath cleaning device according to claim 2, wherein said endoscope sheath cleaning member is a plate-like member of spongy material.

8. The endoscope sheath cleaning device according to claim 7, wherein said endoscope sheath cleaning member comprises a coupling element for connecting the plate-like spongy cleaning member to the rotation means.

9. The endoscope sheath cleaning device according to claim 8, wherein said coupling element is a velvet fastener.

10. The endoscope sheath cleaning device according to claim 1, wherein the rotation means comprises a first disc-like rotating member rotated by a rotational force, and a second disc-like rotating member rotated concentrically with the nozzle head by the first disc-like member.

11. The endoscope sheath cleaning device according to claim 10, wherein said first and second disc-like rotating members are pulleys; and a belt is stretched across both the pulleys.

12. The endoscope sheath cleaning device according to claim 11, wherein said pulleys are of toothed type;

and said belt is of toothed type engageable with toothed pulleys.

13. The endoscope sheath cleaning device according to claim 12, wherein said first and second disc-like rotating members are gear wheels; and an idling gear is provided between the first and second rotating members to transmit the rotational force from the first disc-like rotating member to the second disc-like rotating member.

14. The endoscope sheath cleaning device according to claim 1, wherein said endoscope sheath cleaning means is detachably connected to the rotation means.

15. The endoscope sheath cleaning device according to claim 1, wherein said upper plate of the housing is openable.

* * * * *